United States Patent [19]

Cosman

[11] Patent Number: 4,565,200
[45] Date of Patent: Jan. 21, 1986

[54] UNIVERSAL LESION AND RECORDING ELECTRODE SYSTEM

[76] Inventor: Eric R. Cosman, 872 Concord Ave., Belmont, Mass. 02178

[21] Appl. No.: 374,806

[22] Filed: May 4, 1982

Related U.S. Application Data

[63] Continuation of Ser. No. 190,300, Sep. 24, 1980, abandoned.

[51] Int. Cl.$^4$ ............................................. A61B 17/39
[52] U.S. Cl. .................................... 128/642; 128/736; 128/303.18
[58] Field of Search ...................... 128/303.13, 303.14, 128/303.15, 303.17, 303.18, 642, 736, 784, 786

[56] References Cited

U.S. PATENT DOCUMENTS

| | | | |
|---|---|---|---|
| 2,047,535 | 7/1936 | Wappler | 128/303.17 |
| 3,598,108 | 8/1971 | Jamshidi | 128/303.17 X |
| 3,982,542 | 9/1976 | Ford et al. | 128/303.17 |
| 4,184,492 | 1/1980 | Meinke et al. | 128/303.17 X |
| 4,204,549 | 5/1980 | Paglione | 128/804 |

OTHER PUBLICATIONS

Tew et al., "The Treatment of Trigeminal Neuralgia . . . ", Clinical Neuro, pp. 557–578, 1977.
Tew et al., "Application of Stereotactic Principles . . . ", Appl. Neurophysiol., 41:146–156, 1978.

Primary Examiner—Lee S. Cohen
Attorney, Agent, or Firm—Richard J. Birch

[57] ABSTRACT

A set of instruments is described which enables variability in the size and shape of the region of destructive, radio frequency heating (lesion making) of tissue within the living body, and which enables this variability with only one insertion tract into the body up to the region of the targeted tissue. The set of instruments comprises an entrance cannula with a through-opening along its length and with the through-opening being front-facing at the cannula's distal end, a straight lesion electrode which telescopes into said cannula such that the exposed metal tip of the electrode can extend beyond the distal tip of the cannula by a variable amount, and an off-axis-tipped electrode that also telescopes into the cannula so that its uninsulated tip emerges from the cannula's distal end in an off-axis direction. The bare tips of these electrodes can be raised to a radio frequency (rf) potential by connections on electrode's hubs, this rf potential causing the tissue to heat around the tip. Thus, the surgeon has the option, once the cannula is inserted, of: (i) making a straight lesion volume of variable dimension out the end of the cannula using the straight electrode, or; (ii) enlarging the lesion off-axis in any direction or by any distance using the off-axis electrode. Similar straight or off-axis recording electrodes could be used in place of the above lesion electrodes to record electrical activity of the targeted tissue before or after lesion making.

4 Claims, 8 Drawing Figures

UNIVERSAL LESION AND RECORDING ELECTRODE SYSTEM

CROSS REFERENCE TO RELATED APPLICATION

The present application is a continuation of Ser. No. 190,300 filed Sept. 24, 1980 and now abandoned.

BACKGROUND OF THE INVENTION

A radio frequency (rf) lesion electrode is a device used in electrosurgery, often in neurosurgery, for destroying tissue by heating. It consists typically, as shown in FIG. 1a, of a metal shaft 1, which is insulated with coating 2 over a portion of its length, with a tip 1a that is uninsulated. The shaft 1 and tip 1a are connected to hub 1d, which is usually metal, but may be plastic, and to connector means 5 which enables 1 and 1a to be raised to an rf potential V via connection to an external rf power source 3. When inserted into the living body, and when an inactive or indifferent electrode is connected at another place on the body to carry return current back to 3, then potential V will cause rf current to flow in tissue surrounding tip 1a, this, in turn, causing the tissue to heat up and be selectively destroyed. The destruction zone around tip 1a, called a heat lesion, depends on the size of the tip, the temperature to which the tissue is raised (which is related to V), tissue characteristic, and other factors. The straight electrode like that in FIG. 1a is most common for brain surgery. Manufacturers of such electrodes are Radionics, Inc. (USA), OWL Inst. Ltd., (Canada), F. L. Fischer (W. Germany), Leksell (Sweden), and Vitatron (Netherlands). All straight elecrodes, to date, involve a fixed tip geometry i.e. uninsulated tip length 1 and tip diameter d. Often a temperature sensor is in the tip 1a, and the contact(s) for it 5 are brought out through the hub 1d to connect to external temperature monitoring circuits 7. In this way, the lesion temperature can be monitored while the heat lesion is being made.

Another type of existing straight rf lesion electrode system is shown in FIG. 1b. Here, a metal, uninsulated cannula 11 is inserted into the body, through which an rf electrode, similar to that in FIG. 1a, is inserted. When 11 is connected to ground, it becomes the indifferent electrode, and rf current will flow between it and active rf tip 1a. Such an electrode system has been used for percutaneous cordotomies (rf lesions being made in the spinal cord) for years, and are offered by Radionics, Inc. and OWL, Ltd. As shown in FIG. 1b, by varying the degree of insertion of shaft 1 into cannula 11, one can vary the extension distance x of tip 1a from the tip 11a of 11. However, in all systems to date, the tip exposure length 1 of tip 1a is predetermined and fixed, not to be varied after insertion. Manufacturers offer separate electrodes, with different tip lengths 1 and tip diameters, for different neurosurgical procedures. Radionics, the largest maker of such electrodes, in fact, offers a wide range of types such as in FIG. 1a and FIG. 1b for just that reason.

A third class of rf lesion electrodes exists to date which has a side-outlet tip extension 1c as shown in FIG. 1c. All such electrode systems prior to this invention comprise a cannula 1 which has an occluded front end 1e and a side hole opening 12, through which a flexible tip 1c emerges. Tip 1c may be fully conductive, or partially insulated, and it connects to an inner cannula 15 which telescopes through 1. Outer cannula 1 may have an uninsulated straight tip portion 1a of length 1, or it may be fully insulated. Tip 1c connects to rf potential V, and, thus, can cause rf heating of tissue off the axis of cannula 1. Thus, with a single insertion tract of cannula 1, one has the option of making a straight tip lesion, if tip 1a is uninsulated, or of making an off-axis enlargement of the lesion zone.

At present, there has been one group of researchers and two manufacturers that have reported an electrode as in FIG. 1c, and their objectives for the electrode were restricted to brain surgery. The research group was Zervas, et. al., and the companies are Radionics, Inc. (USA) and F. L. Fischer (W. Germany). Zervas, et. al. and Radionics have reported an electrode for which the entire tip 1c was uninsulated, so that its area may be varied according to extension x. The F. L. Fischer Company has an electrode in which all but the tip end of 1c is uninsulated and in which cannula 15 is insulated from, and thus isolated from, cannula 1, whereby only a portion of tip 1c is active for heating. All of these designs have involved a side-hole cannula, out of which the side extension tip 1c emerges; i.e. they have a forward looking occlusion, as represented by portion 1e in FIG. 1c, in their electrode cannula, and thus they are unable to allow emergence of a straight electrode in the forward direction. The electrode system of FIG. 1c is more versatile than those of FIGS. 1a and 1b, but it still is not as versatile as is required in many neurosurgical contexts. The dimensions of the straight axial tip 1a are fixed; i.e., length 1 and the diameter of 1a are fixed and cannot be changed once the cannula 1 has been inserted into the brain. The off-axis dimension x can be varied by varying the insertion depth x of inner hub 18b relative to outer hub 1d, as in the Zervas and Radionics designs, but there are many situations, as described below, where this does not provide the universal variability of tip dimensions and shapes which is required using a single inserted guide cannula.

It is an object of this invention to provide an electrode system whereby, with a single entrance cannula, and thus with a single entrance tract into the body, one can provide: (a) a straight electrode tip with variable tip length 1 and tip diameter as desired; or, (b) a curved electrode tip which is capable of providing a variable off-axis lesioning tip. Furthermore, the system may be adaptable also to accept both straight and off-axis stimulating and/or physiologic recording electrodes for probing the target area prior to or after lesion-making through the same entrance tract.

BRIEF DESCRIPTION OF THE DRAWINGS

FIGS. 2A through 2D show various embodiments of the present invention with FIGS. 2A and 2B showing a universal rf lesion electrode system with a straight inner electrode device (FIG. 2A) and a flexible tip inner electrode device (FIG. 2B) while FIGS. 2C and 2D depict the additional use of straight and curved recording electrodes (FIGS. 2C and 2D, respectively)

DESCRIPTION OF THE INVENTION

Figure 1A:
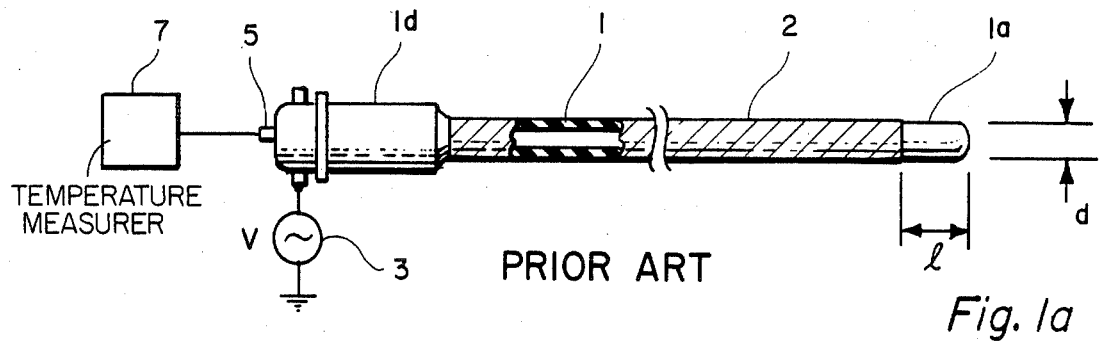
FIGS. 1A, 1B, and 1C show various forms of prior art radio frequency lesion electrodes.
Figure 1B:
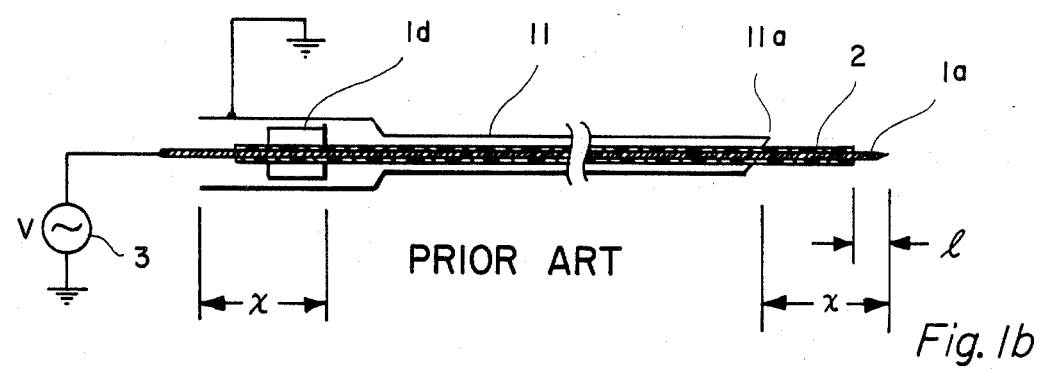
Figure 1C:
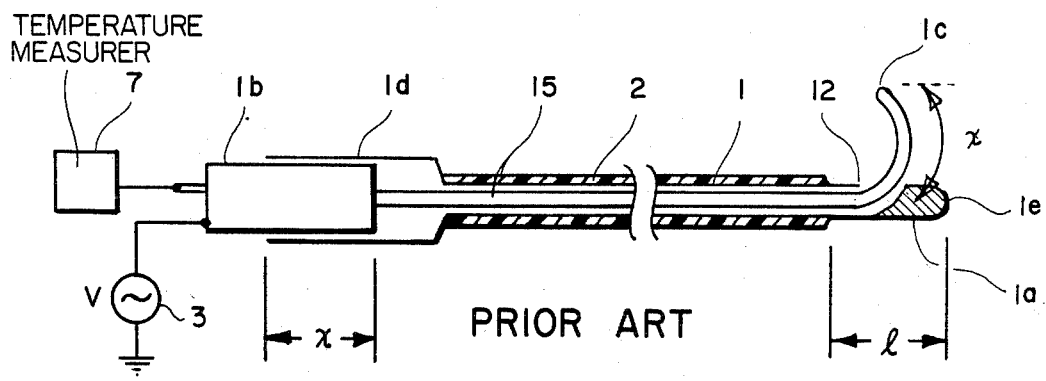
Figure 2A:
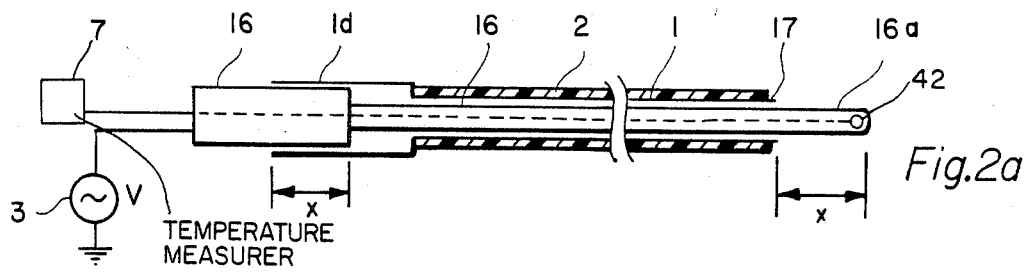
Figure 2B:
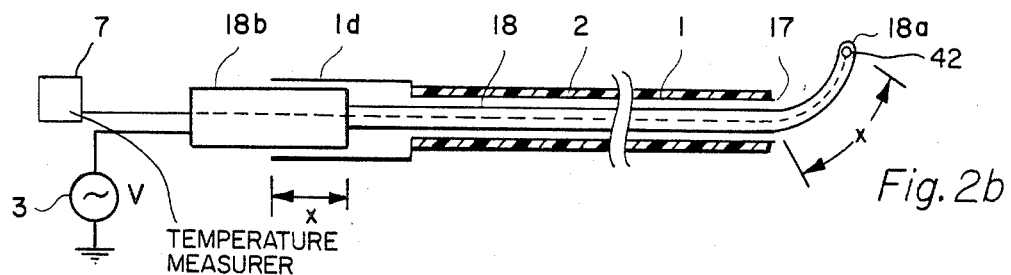

An embodiment of the invention is shown in FIGS. 2a, 2b, 2c, and 2d. FIG. 2a and FIG. 2b show a universal rf lesion electrode system, whereby said above stated objective can be accomplished. The outer entrance cannula 1 serves as an introduction or guide cannula as in FIG. 1c, and is conveniently insulated over most of its length with coating 2. Within 1 telescopes inner cannula 16 which may be made of metal. Cannula 16 is in electrical continuity with its tip 16a which can extend beyond the end of 1. Cannula 1 has a forward looking opening 17 which permits tip 16a to extend straight out from it. By gauging the penetration of inner hub 16b into outer hub 1d, one can vary the amount of extension x of 16a beyond the end 17. Since tip 16a is bare, then its length is a variable-length active lesioning tip, in contrast to FIGS. 1a, and 1b, where the lensioning tip is fixed. FIG. 2b shows the same cannula 1 as in FIG. 2a, but with another element of the electrode system, namely, an inner electrode device which has a flexible curved tip 18a which, when it emerges from front-facing opening 17 in 1, moves in an off-axis direction. The amount of arc length x is variable, dependent on how far hub 18b is into hub 1d. And the asymuthal angle, or rotation angle, of tip 18a emergence is gauged by the relative angular orientation of hub 1d relative to hub 18b.

Thus, with the combined system of a straight, insulated cannula 1 with a forward-facing lumen or opening in its distal end 17, plus a straight electrode 16 which can be inserted into said cannula and having variable tip exposure 16a, and plus a second flexible-tipped electrode 18, the flexible tip 18a of which goes off-axis when it emerges from the outer cannula and for which the degree of emergence of 18a is variable, the surgeon has the flexibility and option, with only one insertion tract into the living body to make a variety of lesion shapes, both straight and off-axis.

There are several long-standing surgical problems which this system now solves. A major one is in the rf lesioning of the trigeminal nerve, where, with one insertion of a straight cannula, it is not possible to reach critical nerve targets off-axis. Previously, this meant having to withdraw and reinsert the cannula, at great pain to the patient, or to get an unsuccessful result altogether. Recently Dr. John Tew and this inventor have submitted a paper to the Journal of Neurosurgery describing a system like that in FIG. 2a and FIG. 2b which solves this problem as described above.

Some constructional details of the Tew-Dosman electrode are that the cannula 1 is made of steel tubing, with a fully insulated exterior, and both shafts 16 and 18 are also made of steel and uninsulated so that they electrically contact cannula 1 when inserted. The tips of 16 and 18, 16a and 18a, respectively, are bare and thus represent active lesioning surfaces with variable exposure length x. Thus, the shaft 1 is inserted only once until its distal end approaches the target. Then, without any further cannula intrusions into the body, the different tip shapes can be made to emerge from the cannula's end-opening to search for the desired target point near the tip of the cannula. The tip of the cannula has an angled bevel, and there is a similarly tipped obdurating stylet which can be inserted into the cannula, so that the cannula can penetrate the skin and tissue easily, when inserted into the body to approach the target, i.e. the trigeminal nerve.

Another important context where this electrode system is of advantage is in making rf lesions in the brain, where it is clear that a minimum number of cannula insertions is esssential.

Variations on the universal rf lesion electrode system of FIGS. 2a and 2b are, of course, possible. Variation of insulation of inner and outer cannulae 1, 16, and 18 are possible to achieve different active tip geometries. Inner electrode 18, may be replaced by an inner electrode system like that in FIG. 1c to achieve other mechanical and geometric effects. The elements 1, 16, and 18 may be combined with, or have built into them, temperature sensors, other stimulating or recording electrode contacts, or movable stimulating and/or recording electrodes or microelectrodes.

We note in connection with the trigeminal nerve procedure, that a relatively small diameter electrode cannula 1 is essential. Typically, a cannula diameter of less than 19 gauge, or 0.042", is needed in this procedure. This is the case in various stereotaxic procedures in the brain as well. It is an advantage of the system of FIG. 2a and 2b, that to achieve the straight and off-axis geometries with only one entrance guide cannula, namely cannula 1, one can minimize the overall diameter of the inserted electrode, as compared to systems where several telescoping cannulae might be used to achieve the same effect. In the trigeminal nerve electrode of Tew and Cosman, mentioned above, the cannula, equivalent to 1 in FIG. 2, is a 19 gauge tube, and the diameters of the tip extensions, equivalent to 16a and 18a in FIGS. 2a and 2b, are 0.7 mm, or 0.032". These are unprecedentedly small dimensions, and are easily achievable because of the construction as in FIGS. 2a and 2b.

Figure 2C:
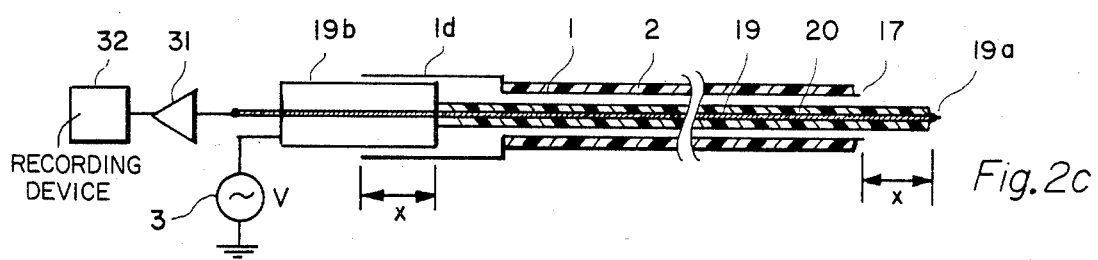
Figure 2D:
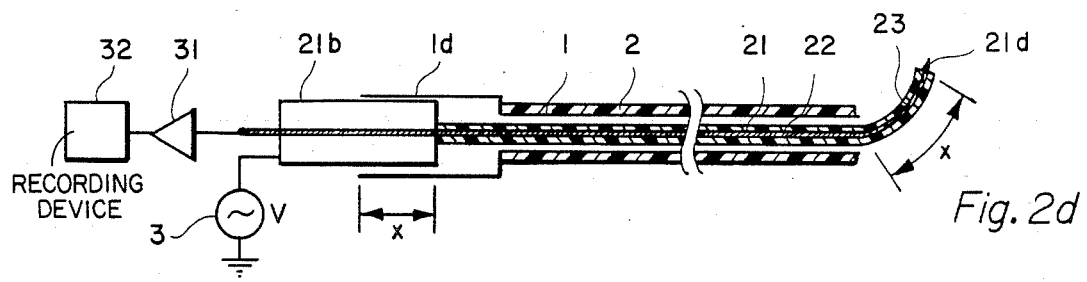

In addition to universal lesion electrode capabilities, the system of FIGS. 2a and 2b may be extended to include further elements to provide universal electrode recording capabilities as well. FIGS. 2c and 2d show means for doing that. In FIG. 2c, the same cannula 1 of FIGS. 2a and 2b is shown, and inserted into it is a straight recording electrode. This electrode has a metal wire 19 which is insulated by coating 20, and there is a bare tip 19a of wire 19 which, when inserted into the brain, can record electrical activity from nerve cells. Recording such activity is often useful to determine regions in the brain where lesions or biopsies must be made. Again, the degree of emergence x of recording tip 19a away from cannula end 17 is determined by the insertion depth of hub 19b into hub 1d.

FIG. 2d shows another recording electrode with a curved tip inserted into cannula 1. This electrode has a wire 21 which is insulated by coating 22, and the distal end 23 of the wire 21 has a resilient curve in it. The insulation 22 over the curved portion is flexible so that, as the wire emerges from the end 17 of cannula 1, then the wire will describe a curved arc. The tip 21a of wire 21 is exposed to record electrical neural activity off the axis of the electrode, and the extension x is gauged by distance x of the hubs relative to each other. External amplifier 31 and recording devices 32 may be attached to electrode 19 to record the tissue potentials. We note, too, that rf lesion potential from 3 may be attached to the same electrodes to create heating of cells or tissue if desired, on the same electrodes 19 and 21.

Thus, with the same insertion of cannula 1 into the body, these straight and curved recording electrodes can be used to probe tissue in the region of the cannula tip 17. Such recording may be made prior to or after episodes of lesion-making, using the electrode systems of FIGS. 2a and 2b. The collection of instruments represented by FIGS. 2a, 2b, 2c, and 2d are, then, a universal recording and lesioning system which minimizes the number of insertions through tissue which lies between the skin and the region of the target within the body.

The very tip end 17 of cannula 1 may have a portion which is uninsulated so that, in a configuration where cannula 1 is insulated from the electrode elements that are inserted into it, then cannula may be attached to the opposite pole of the external electronics, and, thus, tip 17 becomes one side of a bipolar tip geometry relative to the other pole which is the inner element tip.

In use, then, the system of FIGS. 2a, 2b, 2c, and 2d, or any subset thereof, might be applied as follows. Cannula 1, with an obderating stylet (not shown) inserted into it to occlude the opening in its end, is inserted into the body until its tip 17 is near a desired target region. Then, the straight or curved, lesion or recording elements may be successively inserted into cannula 1 to explore and make lesions in tissue in the tip region. Only one major intrusion is made into the body, namely that of the insertion of cannula 1. Prior to this invention, no such universal, minimally-invasive combination of lesion, stimulating, or recording electrodes existed. By making the curvature of the curved lesion and recording tips 18 and 21a the same, one can, by successive extensions of them from tip 17, map out the same region of tissue near the tip 17, and thus perform coordinated lesion and recording procedures on the same tissue, off-axis from the electrode axis.

It may be noted that nearly all stereotaxic guides utilize a guide tube which is held in the guide and through which electrodes of any sort may be passed and directed at a target in the body. However, no such guide cannula as 1 in FIG. 2, designed to reach down to the target itself and which enables through-passage of both straight and side-extending tipped electrode devices, has been devised or anticipated previously. Furthermore, the system of the target-reaching guide cannula 1 of FIG. 2 plus the straight-tipped and off-axis-tipped inner electrodes, as illustrated in FIGS. 2a and 2b or FIGS. 2a, 2b, 2c, and 2d, offer a unique and new universal sterotaxic instrument combination which significantly expands the technical frontier of rf stereotaxic neurosurgery and reduces risk to the patient. Until this invention, all techniques in stereotaxic neurosurgery, which sought to enlarge a lesion volume off the axis and along the axis of the inserted probe, required withdrawing the probe and inserting it in another tract, withdrawing the probe out of the brain and reinserting into the brain a probe of a different type (i.e., side-outlet, different tip length or diameter, etc.), changing the depth of insertion of the probe and making more lesions, or a combination of the above. By means of this invention, such undesirable maneuvers can be avoided.

Figure 3:
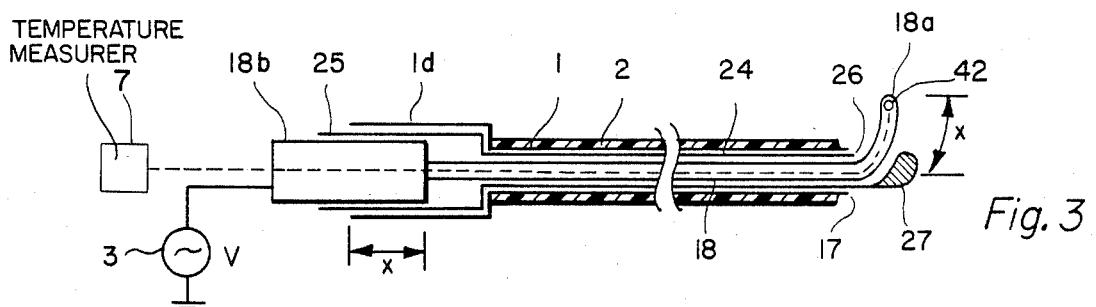
FIG. 3 illustrates another embodiment utilizing an intermediate cannula.
Figure 4:
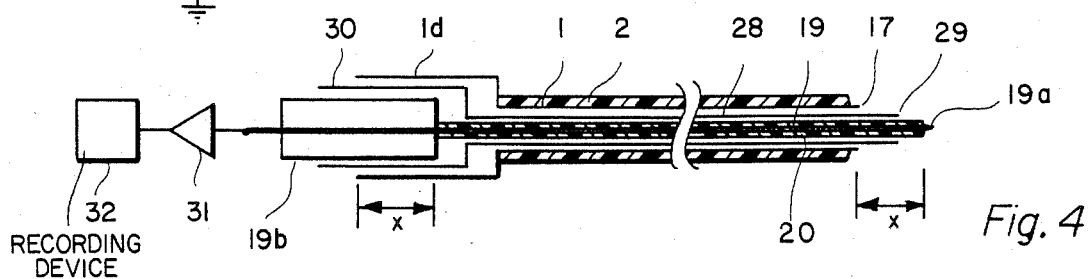
FIG. 4 depicts a variation of FIG. 3 utilizing a different form of the intermediate cannula.

Finally, FIG. 3 and FIG. 4 show some notable variants of the previous embodiments which are intended to be within the scope of this invention. In FIG. 3, a variant of FIG. 2b is shown in which, instead of the off-axis inner electrode means 18b, 18, and 18a which are inserted into entrance cannula 1 as in FIG. 2b, there is another intermediate cannula 24 which goes into entrance cannula 1, cannula 24 having hub 25 and closed end 27 with a side hole 26 at its tip. Inside of cannula 24 is inserted off-axis electrode 18, 18a, and 18b, similar to that in FIG. 2b. Cannula 24 with its sidehole tip design, like the electrode in FIG. 1c, provides a means of deflecting flexible tip 18a off-axis. The relative depth and orientation of hub 18b relative to hub 25 or hub 1d again tells the surgeon the extension of the tip 18a relative to cannula opening 17.

FIG. 4 shows another intermediate cannula variation of the FIG. 2 designs, this time for the example of the straight recording electrode of FIG. 2c. It is a practical problem of the design of FIG. 2c that, to insert inner electrode 19b, 19, 19a into cannula 1, one risks bumping the sharp tip 19a on hub 1d and dulling the former. To avoid this, in FIG. 4, intermediate cannula 28 is used to protect electrode 19b, 19, and 19a as the assembly is inserted into cannula 28, then the assembly 28 plus electrode 19 is inserted into cannula 1, and, once tip 29 of cannula 28 is extended from cannula end 17 by the correct amount, then tip 19a may be pushed out from opening 29 to record tissue potentials.

Similar variations of FIGS. 2a and 2d may be done. Temperature sensors may be installed in the tips of any of the electrodes or cannula shown in FIGS. 2, 3, or 4 for recording lesion or body temperatures. Such temperature sensors are depticted in FIGS. 2A, 2B and 3 and are identified by the reference numeral 42. The temperature sensors 42 are connected to conventional recorders 7. It is obvious, too, that once entrance cannula 1 is inserted into the body so that its distal tip opening 17 is just at the target tissue, then other devices, such as biopsy forceps, biopsy cutters, stimulating electrodes, endoscopes, etc., may be inserted into cannula 1 to perform other operations on the target tissue. These may be usefully done in conjunction with the use of lesion, stimulating, and recording electrodes as shown in FIGS. 2, 3, and 4.

Having described in detail various embodiments of my invention, it will now be apparent to those skilled in the art that numerous modifications can be made therein without departing from the scope of the invention as defined in the following claims.

What I claim and desire to secure by Letters Patent of the United States is:

1. A universal radio frequency heat lesion electrode kit adapted to provide a surgeon with the ability to vary the dimensions and the orientation of heat lesions made within the body with only a single entrance tract into the body, said kit comprising:

(a) an entrance cannula having a hub on its proximal end and a straight elongated shaft that is adapted to be inserted into the living body such that the distal end of said cannula shaft which is the distal end of said cannula can be brought into proximity to target tissue within the living body which is to be destroyed by a heat lesion, said entrance cannula having a through-opening which extends from said proximal end to the distal end of said cannula shaft, the through-opening having a portion which is a straight through-opening such that a straight shaft may be passed completely through it and emerge from said distal end, and said cannula shaft being covered with an insulating material such that at most only a small portion of its surface at said distal end of said shaft is uninsulated;

(b) a straight lesion electrode which is adapted to be inserted into said entrance cannula, the straight lesion electrode having a hub on its proximal end and a straight elongated shaft that is adapted to be inserted through the through-opening of said entrance cannula so that the straight distal tip of said straight lesion electrode can emerge from the through-opening at said distal end of said entrance cannula, at least a portion of the surface of said straight distal tip being metal and uninsulated, said straight metal distal tip being electrically connected to connection means on said hub of said straight lesion electrode, whereby an external source of radio frequency voltage may be connected to the connection means so as to raise said straight metal distal tip to a radio frequency voltage, said straight lesion electrode and said entrance cannula being so adapted that when said straight lesion electrode is inserted into said through-opening of said entrance cannula then said straight distal tip will extend beyond said distal end of said entrance cannula in a straight direction which is parallel to the direction of said cannula shaft, and the amount of said exposed metal surface of said straight distal tip beyond said distal end of said cannula can be varied in accordance with the relative positions of said straight electrode hub and said cannula hub;

(c) an off-axis lesion electrode which is adapted to be inserted into said through-opening of said entrance cannula, the off-axis lesion electrode having a hub on its proximal end and an elongated shaft portion that is adapted to be inserted through said through-opening of said entrance cannula so that the distal tip portion of said off-axis lesion electrode can emerge from said through-opening at the distal end of said entrance cannula, the distal tip of said off-axis lesion electrode being so adapted that when it emerges from said through-opening at said cannula distal end then it can emerge beyond said cannula distal end in a direction which is off the axis of said cannula shaft, at least a portion of the surface of said distal tip of said off-axis lesion electrode being metal and uninsulated, the metal portion of said off-axis lesion electrode tip being electrically connected to connection means on said hub of said off-axis lesion electrode, whereby an external source of radio frequency voltage may be connected to the off-axis electrode connection means so as to raise said metal portion of said off-axis lesion electrode tip to a radio frequency voltage, said off-axis lesion electrode and said entrance cannula being so adapted that when said off-axis lesion electrode is inserted into said through-opening of said entrance cannula then said distal tip of said off-axis lesion electrode will extend out of said through-opening in the distal end of said entrance cannula in a direction which is off the axis of said cannula shaft, and the direction of and the degree of extension of said metal uninsulated portion of said distal tip of said off-axis lesion electrode relative to said distal end of said entrance cannula can be varied in accordance with the relative orientations and positions of said off-axis electrode hub and said cannula hub; and, said off-axis lesion electrode having thermal sensing means for monitoring the temperature of said metal uninsulated portion of said distal tip whereby, when in use, said entrance cannula can be inserted into the living body such that said distal end of said entrance cannula is in proximity to tissue which is to be destroyed by radio frequency heating, and, without any subsequent withdrawal or relocation of said entrance cannula, there are provided the surgical options of:

(1) making an axially symmetric heating of tissue located adjacent to said through-opening in said distal end of said cannula by inserting said straight lesion electrode into said cannula so as to have said straight distal tip extend beyond said cannula distal end into the tissue to be heated and applying said radio frequency voltage to said metal portion of said straight distal tip, thereby causing tissue adjacent to said straight distal tip to be heated, the size of the region of tissue to be heated in the direction of said straight distal tip being chosen by the amount that said straight distal tip is extended beyond said distal end of said cannula; and, (2) making an off-axis heating of tissue located adjacent to said through-opening in said distal end of said cannula by inserting said straight off-axis lesion electrode into said cannula so as to have said off-axis distal tip extend out of said cannula distal end into the tissue to be heated and applying said radio frequency voltage to said metal portion of said off-axis lesion electrode tip, thereby causing tissue adjacent to said off-axis lesion electrode tip to be heated, the size of and the orientation of the region of tissue to be heated off of the direction of the axis of said entrance cannula shaft being chosen by the amount that said off-axis electrode tip is extended from said distal end of said cannula and by the direction in which said off-axis electrode is extended from said distal end of said cannula as determined by the relative position and orientation of said hubs of said cannula and said off-axis electrode and, the temperature of the region surrounding the distal tip can be monitored.

2. The electrode kit of claim 1 wherein said straight elongated shaft of said entrance cannula comprises a straight metal tube with an open distal end, said straight elongated shaft of said straight lesion electrode comprises a straight metal tube the distal tip surface of which is uninsulated and is the distal tip end of said straight electrode, said hub of said straight electrode is in part metal and is electrically connected to said straight metal tube, said elongated shaft of said off-axis lesion electrode comprises a metal tube element and said distal tip of said off-axis electrode comprises a flexible curved metal element which is connected to said metal tube element of said off-axis electrode so that when said off-axis electrode is inserted into said through-opening of said cannula then said curved metal element will emerge out of said distal tip of said cannula in an off-axis direction, said hub of said off-axis electrode being in part metal and electrically connected to said curved metal element by said metal tube element.

3. The electrode kit of claim 1 wherein said entrance cannula, said straight lesion electrode, and said off-axis lesion electrode are sized for percutaneous heat lesion making in the trigeminal nerve, and whereby with one insertion into the trigeminal nerve with said entrance cannula, the surgeon has the option of making a straight variable length lesion in the trigeminal nerve or an off-axis lesion into off-axis regions of the trigeminal nerve so as to achieve more specific areas of pain relief.

4. The kit of claim 1 and further including a recording electrodes adapted to enable the surgeon to record electrical activity of tissue in the region around said through-opening in said distal end of said entrance cannula, said recording electrodes comprising:

(a) a straight recording electrode which is adapted to be inserted into said entrance cannula, the straight recording electrode having a hub on its proximal end and a straight elongated shaft that is adapted to be inserted through said through-opening of said entrance cannula so that the straight distal tip of said straight recording electrode will emerge from the through-opening at said distal end of said entrance cannula, in a straight direction which is parallel to the direction of said cannula shaft, said straight shaft of said straight recording electrode comprising a conductive element which runs from the distal end to the proximal end of said straight recording electrode shaft and connects on the proximal end with recording connection means on said hub of said straight recording electrode and connects on the distal end with an uninsulated metal recording tip, said straight recording electrode being insulated over a portion of its surface sufficiently to insulate it from said entrance cannula when inserted into said entrance cannula, said recording connection means being adapted to provide connection means to external recording apparatus, whereby, when in use and said entrance cannula is inserted into the living body, said straight recording electrode recording tip can be made to extend out beyond said cannula distal tip in a straight direction, thus enabling recording of electrical activity in tissue which is located in said straight direction; and, (b) an off-axis recording electrode which is adapted to be inserted into said entrance cannula, the off-axis recording electrode having a hub on its proximal end and an elongated shaft portion that is adapted to be inserted through said through-opening of said entrance cannula so that the distal tip portion of said off-axis recording electrode can emerge from said through-opening at the distal end of said entrance cannula, the distal tip of said off-axis lesion electrode being so adapted that when it emerges from said through-opening at said cannula distal end then it emerges beyond said cannula distal end in a direction which is off the axis of said cannula shaft, said distal tip end of said off-axis recording electrode having an uninsulated metal recording tip portion which is electrically connected by electrical conductor means which runs along said elongated shaft portion to recording connection means in the hub of said off-axis recording electrode, said off-axis recording electrode being insulated over a portion of its surface sufficiently to insulate it from said entrance cannula when inserted into said entrance cannula, said recording connection means on said off-axis recording electrode hub being adapted to provide connection means to external recording apparatus, whereby, when in use and said entrance cannula is inserted into the living body, said metal recording tip portion of said distal tip of said off-axis recording electrode can be made to extend out beyond said entrance cannula distal tip in a direction which is off the axis of said entrance cannula, thus enabling recording of electrical activity in tissue which is located on regions which are in the vicinity of said cannula distal tip and which are off the axis of said entrance cannula.

* * * * *